United States Patent [19]
Gupta

[11] Patent Number: 5,343,045
[45] Date of Patent: Aug. 30, 1994

[54] METHOD AND DEVICE FOR MEASURING MOISTURE CONTENT

[75] Inventor: Bal K. Gupta, Etobicoke, Canada

[73] Assignee: Ontario Hydro, Toronto, Canada

[21] Appl. No.: 75,093

[22] Filed: Jun. 11, 1993

[51] Int. Cl.⁵ .......................................... G01N 21/49
[52] U.S. Cl. .................... 250/339.1; 250/341; 250/227.23; 356/418
[58] Field of Search ............... 250/339, 341, 227.33, 250/227.18; 356/418, 419

[56] References Cited

U.S. PATENT DOCUMENTS

| | | |
|---|---|---|
| 4,221,962 | 9/1980 | Black et al. . |
| 4,266,878 | 5/1981 | Aver ........................ 250/255 |
| 4,497,577 | 2/1985 | Sato et al. .................. 250/227.23 |
| 4,498,004 | 2/1985 | Adolfsson et al. . |
| 4,599,711 | 7/1986 | Cuomo . |
| 4,634,856 | 1/1987 | Kirkham . |
| 4,764,018 | 8/1988 | Inoue ........................ 356/418 |
| 4,894,532 | 1/1990 | Peterson et al. ............. 250/227.23 |
| 4,910,402 | 3/1990 | McMillan ................... 250/341 |
| 4,929,847 | 5/1990 | Yamazoe et al. . |
| 4,945,230 | 7/1990 | Saaski et al. ............... 250/227.23 |
| 5,005,005 | 4/1991 | Brossia et al. . |
| 5,054,487 | 10/1991 | Clarke ..................... 250/227.23 |
| 5,070,874 | 12/1991 | Barnes et al. ............... 250/339 |
| 5,239,180 | 8/1993 | Clarke .................... 250/341 |

*Primary Examiner*—Paul M. Dzierzynski
*Assistant Examiner*—Drew A. Dunn
*Attorney, Agent, or Firm*—Ridout & Maybee

[57] ABSTRACT

A device for measuring the moisture content of an absorbent material, for example the paper insulation in an electrical transformer, uses a back scattered radiation technique to determine the absorption of light at specific wavelengths. A ratio of the back scattered radiation at different wavelengths can be compared against known values corresponding to a specific moisture content. An optical waveguide such as a bifurcated optical fibre is provided with a probe end optically coupled to a source end and a detection end, for transmitting light to the absorbent material and transmitting back scattered radiation to a detector.

12 Claims, 3 Drawing Sheets

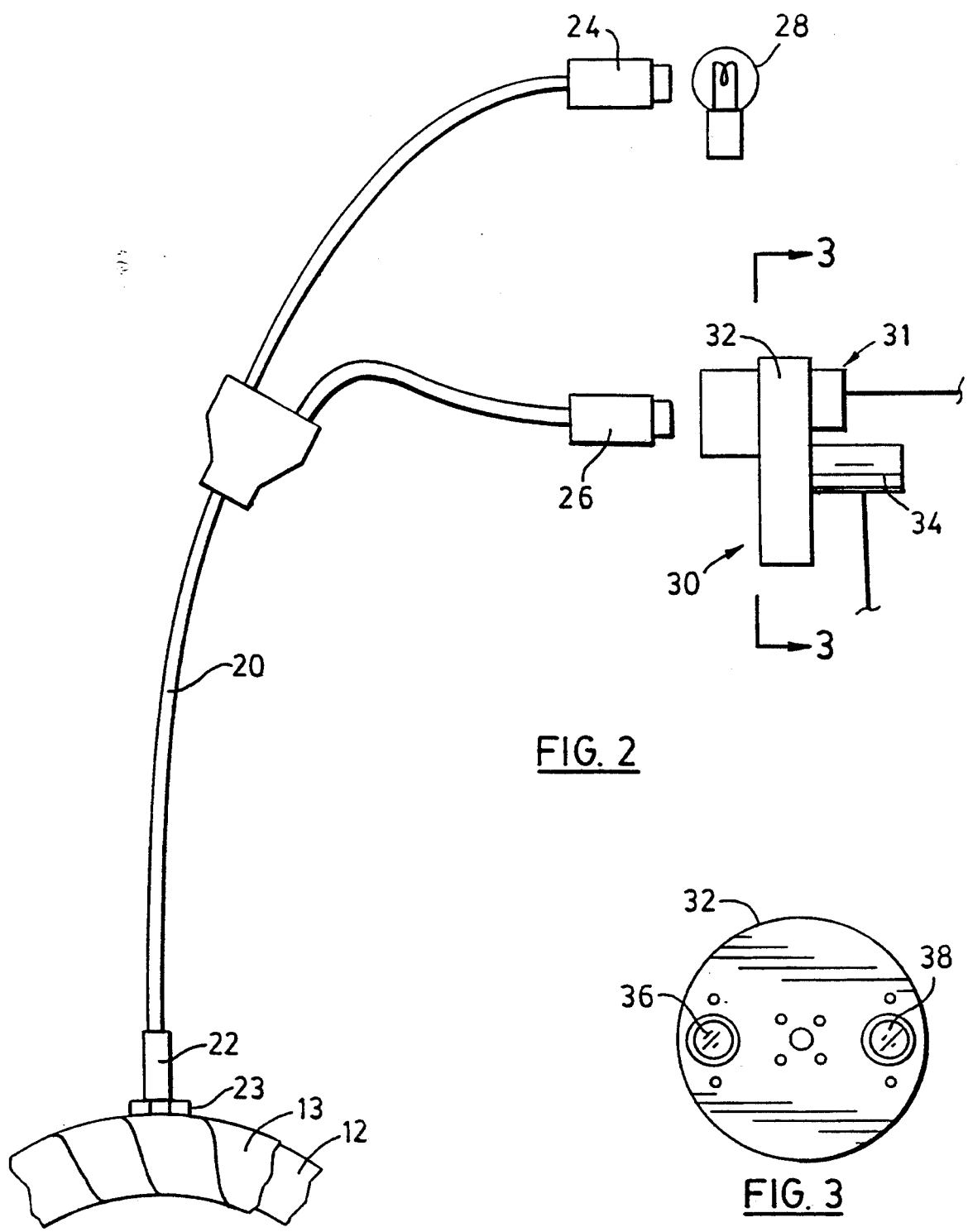

METHOD AND DEVICE FOR MEASURING MOISTURE CONTENT

FIELD OF THE INVENTION

This invention relates to a method and device for measuring moisture content of an absorbent material which is not easily accessible for measurements. In particular, this invention relates to a method and device for measuring the moisture content of paper insulation used in electrical transformers filled with material oil or synthetic fluids.

BACKGROUND OF THE INVENTION

High voltage transformers contain paper insulated conductors immersed in an oil-filled tank. During the manufacturing process, the moisture content of the paper insulation is reduced to less than 0.5 percent. However, as a transformer ages, the moisture content of the paper may gradually increase as moisture slowly diffuses from the atmosphere into the oil, and then into the paper insulation. Excessive moisture content in paper insulation quickly deteriorates its insulating ability, reducing the electrical resistance of the insulation and promoting local heating and surface tracking under operating electrical stress.

Moreover, under thermal stress as experienced either during normal operation or during emergency overloading of a transformer, excess water molecules may be converted into free gas bubbles, which under electrical stress will produce partial discharges that gradually degrade the oil-paper insulation. Free water molecules are generated when the paper insulation degrades, resulting in a vicious cycle: an increase in the moisture content of the paper above about 2 percent can lead to additional local overheating, gassing, increased partial discharge activity, more water generation, and eventually run away loss in the integrity of the insulation system resulting in a premature failure of the equipment.

During manufacturing, a dissipation factor at 60 Hz of the overall insulation system, either between the primary and secondary windings of the transformer or between a winding and the tank, is used to determine the "dryness" of insulation. For transformers in service, the moisture content in the paper insulation is estimated through measurement of the water content of the transformer oil. However, in both cases the moisture content of the paper insulation cannot be known exactly. Until the present invention there were no practical methods available for direct on-site measurement of moisture content of the paper insulation in transformers.

The present invention provides a method and device for directly measuring the moisture content of paper insulation in electrical transformers. The invention can be used to control "dryness" of the paper insulation in the manufacturing process, resulting in a better product. Furthermore, use of the subject invention can reduce maintenance costs through prevention of unnecessary treatment of transformer insulation, can improve the reliability of power transformers, and can permit full use of the normal capacity and emergency overloading capability of transformers without excessive aging. The method and device of the subject invention can be used to directly measure the moisture content of any absorbent material, the paper insulation in a transformer being an illustrative example.

The present invention utilizes an infrared absorption technique to measure moisture content. A water molecule has many absorption bands in the infrared region of the electromagnetic spectrum. Absorption in any of these bands can be used to determine the moisture content in a sample. For example, water exhibits almost no absorption of radiation at 1.81 $\mu$m and pronounced absorption at 1.92 $\mu$m. The moisture content in a sample can therefore be measured using a back scattered radiation technique, i.e. by taking the ratio of the back scattered radiation at these two wavelengths to provide a direct measurement of the moisture content of the paper insulation.

In the present invention, an optical waveguide such as an optical fibre bundle is used to transmit radiation to and from the paper insulation. The end of the optical fibre is maintained close to, but not in contact with, the paper insulation, which prevents excessive absorption of the radiation by oil. This permits the moisture content to be determined directly in the paper insulation, on-site and without draining the transformer oil. Furthermore, by keeping the optical fibre bundle totally free of metal, the method and device of the present invention can be used in equipment on line, i.e. equipment energized to a high electric voltage, without any interruption in service.

This method of measuring moisture is most suitable and beneficial for absorbent materials that are not easily accessible. Also the method is non-destructive, in that no piece or sample is taken out of the absorbent material.

SUMMARY OF THE INVENTION

The present invention provides a device for measuring moisture content of an absorbent material, comprising an optical waveguide having a probe end optically coupled to source and detection ends, a source of electromagnetic radiation optically coupled to the source end of the optical waveguide, and means for measuring the flux of selected wavelengths optically coupled to the detection end of the optical waveguide, including a detector for measuring and means for displaying, recording or conveying a measurement of the flux of electromagnetic radiation emitted from the detection end of the waveguide at the selected wavelengths.

The present invention further provides a method of measuring the moisture content of an absorbent material utilizing an optical waveguide having a probe end optically coupled to a source end and a detection end, comprising the steps of locating the probe end close to the material, transmitting electromagnetic radiation from the source end to the probe end and from the probe end to the detector end, detecting and measuring the flux values of at least two selected frequencies of electromagnetic radiation emitted from the detection end, and computing or calculating a ratio of the measured flux values and comparing the ratio to a pre-ascertained ratio corresponding to a known moisture content.

The present invention further provides a method of measuring the moisture content of absorbent material immersed in oil or synthetic fluid in electrical equipment, utilizing an optical waveguide having a probe end optically coupled to a source end and a detection end, comprising the steps of locating the probe end close to the absorbent material, transmitting electromagnetic radiation from the source end to the probe end and from the probe end to the detector end, detecting and measuring the flux values of at least two selected frequencies of electromagnetic radiation emitted from the detection end, and computing or calculating a ratio of the measured flux values and comparing the ratio to a pre-ascertained ratio corresponding to a known moisture content.

BRIEF DESCRIPTION OF THE DRAWINGS

In drawings which illustrate by way of example only a preferred embodiment of the subject invention.

FIG. 2 is a perspective view of the preferred form of optical waveguide;

FIG. 3 is an elevation of the optical chopper disc; and

DETAILED DESCRIPTION OF THE INVENTION

Figure 1:
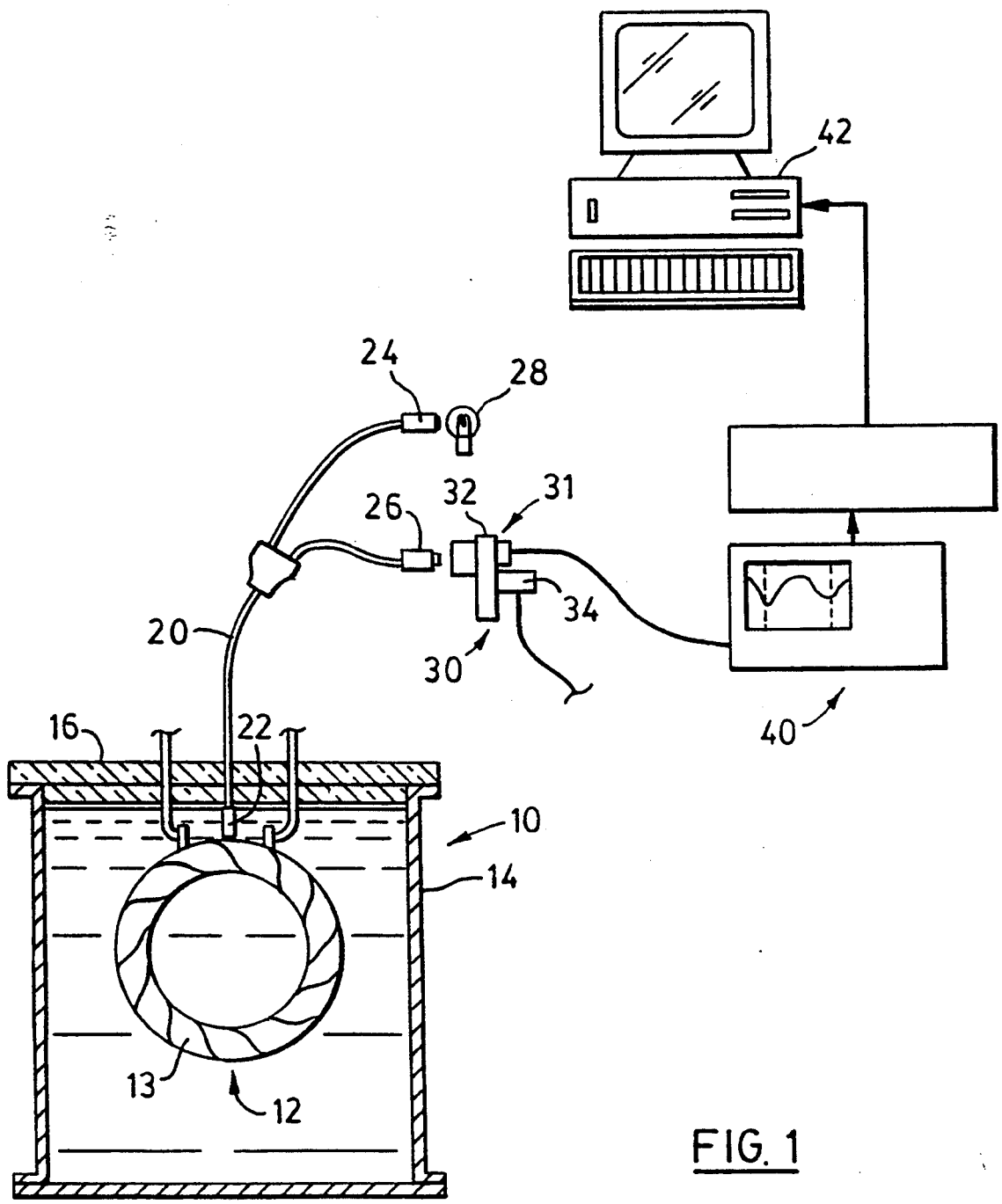
FIG. 1 is a diagrammatic representation of the device embodying the subject invention.

The device for measuring moisture content is illustrated in FIG. 1. The invention will be described using the example of paper insulation in a transformer model 10.

A transformer 10 consists of a transformer coil 12 immersed in oil contained in a gastight tank 14 having an insulating top 16. The transformer coil 12 is wrapped in insulating paper 13.

An optical waveguide 20, preferably a bifurcated, non-metallic optical fibre bundle, comprises a probe end 22 optically coupled to both a source end 24 and a detection end 26. As illustrated in FIG. 2, the probe end 22 is provided with a spacer 23 to maintain the probe end 22 close to, but not in contact with, the paper insulation 13 of the coil 12. For proper functioning of the method and device, the optical fibres must be practically free of residual moisture.

The source end 24 is optically coupled to an infrared radiation source 28, and the detection end 26 is optically coupled to an optical chopper 30 which intercepts radiation falling on an infrared detector 31. The detector 31 is electrically connected to a display device 40, such as a digital oscilloscope, for displaying a measurement of the flux of infrared radiation emitted from the detection end 26 of the waveguide 20. Preferably the detector 31 is also coupled to means for computing and recording the ratio of flux at two selected wavelengths, such as a computer 42 or other data acquisition device.

The optical chopper 30 is provided with optical filters 36, 38 for filtering light of different wavelengths, the wavelengths being selected to provide a discernable contrast in the flux detected by the detector in presence of high moisture content. The filters are located on a chopper disc 32 driven by a motor 34.

Figure 4:
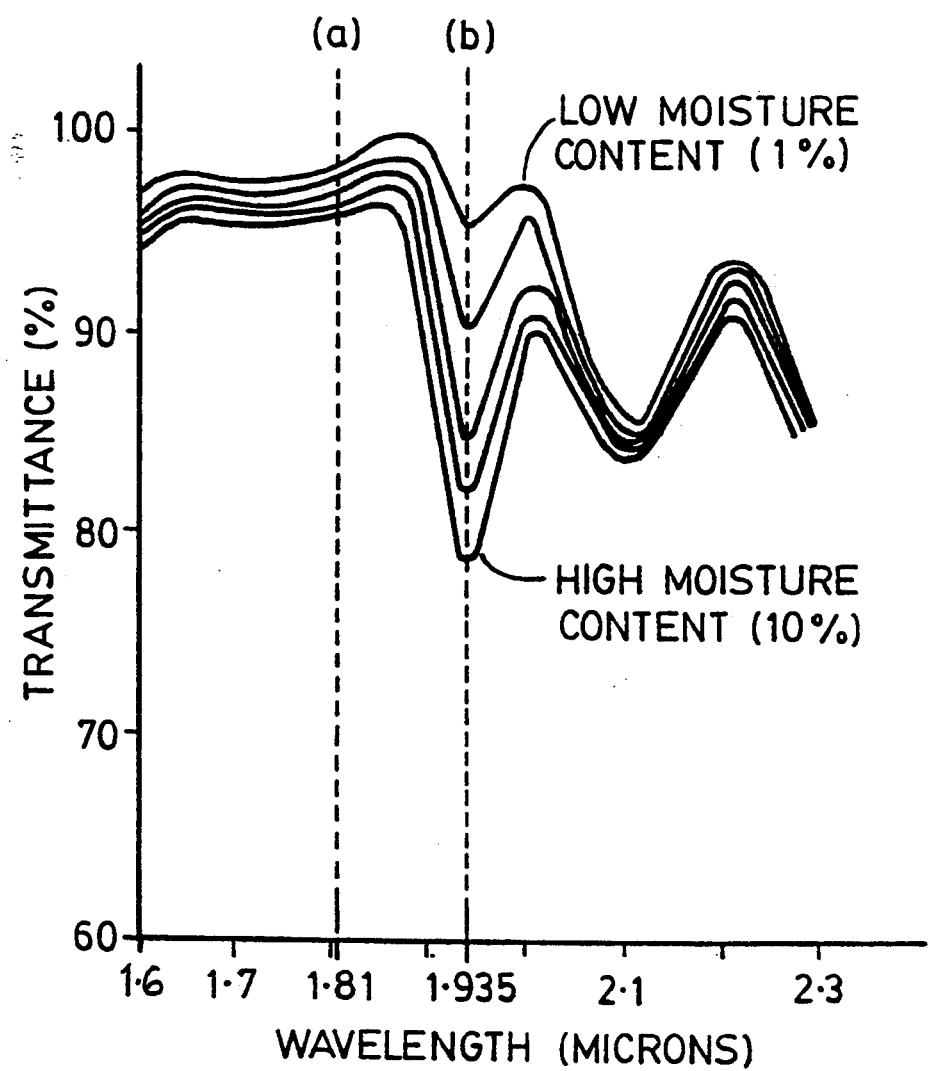
FIG. 4 is a chart illustrating representative levels of absorption of infrared radiation for selected percentages of moisture content.

For example, it can be seen from FIG. 4 that water molecules absorb almost no electromagnetic radiation at a wavelength of 1.81 $\mu$m, but absorption is pronounced at a wavelength of 1.92 $\mu$m. Thus, in a preferred embodiment the filters 36, 38 are selected at 1.81 $\mu$m and 1.92 $\mu$m, respectively.

The method of using the device of the subject invention will now be described. The probe end 22 of the optical fibre 20 is immersed in the tank 14, and the spacer 23 is positioned in contact with the insulating paper 13 of the transformer coil 12. The light source 28, which includes wavelengths in the infrared portion of the electromagnetic spectrum, is activated, thereby transmitting light into the source end 24 of the optical fibre 20. Light travels through the optical fibre 20 to the probe end 22 where it is emitted and strikes the insulating paper 13. The light is reflected, i.e. "back scattered", and re-enters the probe end 22, propagating along the optical fibre 20 until it is emitted from the detection end 26 where it is filtered by the optical chopper 30.

The detector 31 detects alternately, at intervals set by the speed of the chopper motor 34, the flux of back scattered light at the filtered wavelengths, and displays a measurement of the respective flux values on the oscilloscope 40. This information is conveyed to computing and/or recording means such as a data acquisition computer 42, to compute and record the ratio of the flux values. The computer then uses the computed ratio to correlate with known values for moisture content corresponding to that ratio.

It will be apparent that the device embodying the subject invention is portable, and can be used in the field to measure the moisture content of paper insulation 13 with minimum disassembly of the transformer 10. It will further be appreciated that so long as the optical waveguide 20 is completely metal free, service personnel taking the proper precautions can measure the moisture content of the paper insulation 13 without de-energizing the transformer 10, and thus without any interruption in electrical service to the affected region.

It will also be apparent that computing the ratio of flux values by computer 42, although preferred, is unnecessary. A real time measurement of moisture content can be obtained through mental or manual calculation of the ratio of flux values displayed on the oscilloscope 40, and comparison against a table or chart of known values will provide the corresponding moisture content.

The manner of displaying, conveying and recording the flux values of back scattered radiation is entirely conventional. Moreover, certain modifications and adaptations as will be obvious to those skilled in the art may be made to the present invention without departing from the scope thereof, as set out in the appended claims.

I claim:

1. A device for measuring moisture content of an absorbent material, comprising an optical waveguide having a probe end optically coupled to source and detection ends, a source of electromagnetic radiation optically coupled to the source end of the optical waveguide, and means for measuring the flux of selected wavelengths optically coupled to the detection end of the optical waveguide, including a detector for measuring and means for displaying, recording or conveying a measurement of the flux of electromagnetic radiation emitted from the detection end of the waveguide at the selected wavelengths, wherein the means for measuring the flux comprises an optical chopper provided with a first optical filter for transmitting a first wavelength of electromagnetic radiation to the detector and a second optical filter for transmitting a second wavelength of electromagnetic radiation to the detector, the first wavelength being a wavelength at which absorption by water molecules is low and the second wavelength being a wavelength at which absorption by water molecules is high, the optical chopper including means for alternately interposing the first filter and the second filter between the detection end of the optical waveguide and the detector.

2. The device claimed in claim 1 wherein the optical waveguide comprises a bifurcated optical fibre.

3. The device claimed in claim 1 wherein the probe end of the optical waveguide is provided with a spacer.

4. The device claimed in claim 1 wherein the detector comprises a photoconductive sensor.

5. The device claimed in claim 4 wherein the wavelength transmitted by the first filter is 1.81 μm and the wavelength transmitted by the second filter is 1.92 μm.

6. The device claimed in claim 1 further including a data acquisition computer for recording flux values measured by the detector.

7. A method of measuring the moisture content of an absorbent material utilizing an optical waveguide having a probe end optically coupled to a source end and a detection end, comprising the steps of locating the probe end close to the material, transmitting electromagnetic radiation from the source end to the probe end and from the probe end to the detector end, employing an optical chopper and thereby, alternately detecting and measuring the flux values of two selected frequencies of electromagnetic radiation emitted from the detection end, the two selected frequencies of electromagnetic radiation corresponding to a first frequency which exhibits low absorption by water molecules and a second frequency which exhibits high absorption by water molecules and computing or calculating a ratio of the measured flux values and comparing the ratio to a pre-ascertained ratio corresponding to a known moisture content.

8. The method claimed in claim 7 wherein the optical waveguide comprises a bifurcated optical fibre.

9. The method claimed in claim 7 wherein the probe end of the optical waveguide includes a spacer for contacting the material.

10. The method claimed in claim 7 wherein the selected wavelengths are in the infrared region of the electromagnetic spectrum.

11. The method claimed in claim 10 wherein the selected wavelengths are 1.81 μm and 1.92 μm.

12. The method claimed in claim 10 wherein the selected wavelengths are at or close to other absorption wavelengths of water.

* * * * *